United States Patent [19]

Butler et al.

[11] Patent Number: 5,446,054
[45] Date of Patent: Aug. 29, 1995

[54] PROCESS FOR TRANS-6-[2-(SUBSTITUTED-PYRROL-1-YL)ALKYL]PYRAN-2-ONE INHIBITORS OF CHOLESTEROL SYNTHESIS

[75] Inventors: Donald E. Butler, Holland; Tung V. Le, Jenison; Thomas N. Nanninga, Holland, all of Mich.

[73] Assignee: Warner-Lambert Company, Morris Plains, N.J.

[21] Appl. No.: 323,291

[22] Filed: Oct. 14, 1994

Related U.S. Application Data

[62] Division of Ser. No. 243,673, May 16, 1994, which is a division of Ser. No. 135,385, Oct. 12, 1993, Pat. No. 5,342,952, which is a division of Ser. No. 25,701, Mar. 3, 1993, Pat. No. 5,298,627.

[51] Int. Cl.$^6$ .................. A61K 31/40; A61K 31/44; A61K 31/445; C07D 211/14
[52] U.S. Cl. .................. 514/326; 514/343; 514/422; 514/423; 514/427; 514/183; 514/212; 514/235.5; 540/480; 540/602; 544/141; 546/208; 546/281; 548/400; 548/518; 548/523; 548/537; 548/540; 548/560; 548/561; 548/562
[58] Field of Search .................. 546/208, 281; 514/326, 514/235.5, 183, 212, 422, 423, 427, 343; 548/537, 400, 518, 523, 540, 560, 561, 562; 544/141; 540/480, 602

[56] References Cited

U.S. PATENT DOCUMENTS

| | | | |
|---|---|---|---|
| 4,647,576 | 3/1987 | Hoefle et al. | 514/422 |
| 4,681,893 | 7/1987 | Roth | 514/422 |
| 5,003,080 | 3/1991 | Butler et al. | 548/517 |
| 5,097,045 | 3/1992 | Butler et al. | 549/373 |
| 5,103,024 | 4/1992 | Millar et al. | 549/373 |
| 5,124,482 | 6/1992 | Butler et al. | 564/169 |
| 5,149,837 | 9/1992 | Butler et al. | 549/333 |
| 5,155,251 | 10/1992 | Butler et al. | 558/442 |
| 5,273,995 | 12/1993 | Roth | 548/537 |
| 5,276,037 | 1/1994 | Dowell et al. | 514/253 |

OTHER PUBLICATIONS

Tetrahedron Letters, vol. 33, No. 17, pp. 2283–2284 1992, K. L. Baumann, et al.
Tetrahedron Letters, vol. 33, No. 17, pp. 2279–2282 1992, P. L. Brower, et al.
J. Med. Chem., 34, 357–366, Inhibitors of . . . Pyrrole Nucleus, Roth et al., 1991.
CA 115:135870x Inhibitors . . . Pyrrole nucleus. Roth et al., p. 959, 1991.
CA 115:29107u Preparation of . . . Salts thereof. Roth pp. 753–754, 1991.

Primary Examiner—Joseph K. McKane
Attorney, Agent, or Firm—Francis J. Tinney

[57] ABSTRACT

An improved process for the preparation of trans-6-[2-(substituted-pyrrole-1-yl)alkyl]pyran-2-ones by a novel synthesis is described where α-metalated N,N-disubstituted acetamide is converted in seven operations to the desired products, and specifically, a process for preparing (2R-trans)-5-(4-fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide, as well as other valuable intermediates used in the processes and prodrugs which are bioconverted to hypolipidemic and hypocholesterolemic agents and pharmaceutical compositions of the same.

9 Claims, No Drawings

PROCESS FOR TRANS-6-[2-(SUBSTITUTED-PYRROL-1-YL)AL-KYL]PYRAN-2-ONE INHIBITORS OF CHOLESTEROL SYNTHESIS

This is a divisional application of U.S. Ser. No. 08/243,673, filed May 16, 1994, which is a divisional application of U.S. Ser. No. 08/135,385, filed Oct. 12, 1993, now U.S. Pat. No. 5,342,952, granted Aug. 30, 1994, which is a divisional application of U.S. Ser. No. 08/025,701 filed Mar. 3, 1993, now U.S. Pat. No. 5,298,627 granted Mar. 29, 1994.

BACKGROUND OF THE INVENTION

U.S. Pat. No. 4 647 576 which is herein incorporated by reference, discloses certain trans-6-[2-(substituted-pyrrol-1-yl)alkyl]pyran-2-ones.

U.S. Pat. No. 4,681,893, which is herein incorporated by reference, discloses certain trans-6-[2-(3- or 4-carboxamido-substituted-pyrrol-1-yl)alkyl]-4-hydroxy-pyran-2-ones.

The compounds disclosed in the above United States patents are useful as inhibitors of the enzyme 3-hydroxy-3-methylglutaryl-coenzyme A reductase (HMG-CoA reductase) and are thus useful hypolipidemic and hypocholesterolemic agents. Particularly valuable as hypolipidemic and hypocholesterolemic agents are trans(±)-5-(4-fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide and (2R- trans)-5- (4- fluorophenyl) -2- (1-methylethyl) -N, 4-diphenyl-1- [2-(tetrahydro-4-hydroxy-6-oxo-2H-pyran-2-yl)ethyl]-1H-pyrrole-3-carboxamide. The aforementioned compounds have been prepared by a linear synthetic route which employed two reactions conducted at low temperatures (−78° C.) under carefully controlled conditions. The two reactions included the addition of ethyl acetoacetate to an aldehyde and the reduction of the hydroxy ketone produced in this reaction with sodium borohydride and a trialkylborane. Although these reactions provide the target compounds in high diastereomeric excess, they are difficult to conduct on large-scale and use expensive reagents which are difficult to handle. They also do not produce enantiomerically pure products. The materials produced by this method can be separated into enantiomerically pure products but the process is very expensive, time-consuming, and results in the loss of more than 50% of the starting material.

The aforementioned compounds have also been prepared by a linear synthetic route which employed two reactions conducted at low temperatures (−78° C.) under carefully controlled conditions. The two reactions included the addition of the dianion of (S)-1,1,2-triphenylethanediol 2-acetate to an aldehyde and from the product conversion to the hydroxy ketone followed by the reduction of the hydroxy ketone produced in this reaction with sodium borohydride and a trialkylborane. Although these reactions provide the target compounds in high diastereomeric excess and reasonable enantiomeric excess (85:15), they are difficult to conduct on large-scale and use expensive reagents which are difficult to handle. Also, since an 85:15 ratio of enantiomers is produced, extensive chromatography is needed to isolate the desired enantiomer because the racemic product crystallizes leaving the desired isomer in the oily mother liquors. Both these linear procedures were published by Roth, et al, *J Med Chem* 1991;34:356–366.

The aforementioned compounds have also been prepared by a superior convergent route disclosed in the following U.S. Pat. Nos. 5,003,080; 5,097,045; 5,103,024; 5,124,482; and 5,149,837; which are herein incorporated by reference and Baumann KL, Butler DE, Deering CF, et al, *Tetrahedron Letters* 1992;33:2283–2284.

One of the critical intermediates disclosed in U.S. Pat. No. 5,097,045 has also been produced using novel chemistry, as disclosed in U.S. Pat. No. 5,155,251, which is herein incorporated by reference and Brower PL, Butler DE, Deering CF, et al, *Tetrahedron Letters* 1992;33:2279–2282.

The object of the present invention is an improved process for preparing the compounds described above by using a novel synthesis incorporating novel intermediates synthesized using novel chemistry.

Di-lithio and di-potassio-phenylacetamide and phenyl-acetanilide were reported in 1964 to react with ketones and methyl benzoate in liquid ammonia (Work S, Bryant D, Hauser CR, *J Org Chem* 1964;29:722–724).

Solutions of α-sodio N,N-dimethylacetamide and some related α-sodio N,N-dialkylamides were reported in 1966 (Gassman P, Fox B, *J Org Chem* 1966;31:982–983 and Needles H, Whitfield RE, *J Org Chem* 1966;31:989–990).

Solutions of α-lithio N,N-dimethylacetamide and some related α-lithio N,N-dimethylamides were reported in 1977 (Hullot P, Cuvigny T, Larchevêque M, Normant H, *Can J Chem* 1977;55:266–273 and Woodbury RP, Rathke MW, *J Org Chem* 1977;42:1688–1690). These anions have been reacted as nucleophiles with highly reactive substances such as alkyl halides (iodides and bromides), epoxides, aldehydes and ketones. Reaction of these anions with esters appear to have been neglected or not reported. Two references to the reaction of acetamide with methyl benzoate, which proceed through the dianion of N-benzoylacetamide with methyl benzoate, have been found that yielded N-benzoyl benzoylacetamide (Structure A) at relatively high temperatures (Wolfe J, Timitsis G, *J Org Chem* 1968;33:894 and Agami C, *Bull Soc Chim Fr* 1968:1205).

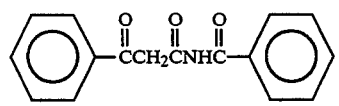

Structure A

We have unexpectedly and surprisingly found that while a solution of α-lithio N,N-dimethylacetamide does not yield any detectable desired product when reacted with (R) 5-cyano-3-hydroxybutyric acid alkyl esters (Formula A), solutions of α-metallo N,N-dialkylacetamide where at least one of the N,N-dialkyl substituents is larger than methyl or the N,N-dialkyl substituents together are cyclic, react at the ester group of (R) 5-cyano-3-hydroxybutyric acid alkyl esters (Formula A).

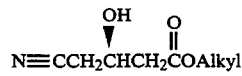

A

Thus, we have unexpectedly found a broad series of novel intermediates that can be used to synthesize the particularly valuable hypolipidemic and hypocholesterolemic agents trans (+)-5-(4-fluorophenyl)-2-(1-methylethyl)-N,4-diphenyl-1-[2-(tetrahydro-4-hydroxy-6-oxo- 2H-pyran-2-yl)ethyl]- 1H-pyrrole-3-carboxamide and (2R- trans)-5-(4-fluorophenyl)-2-(1-methylethyl)N,4-diphenyl-1-[2-(tetrahydro-4-hydroxy-6-oxo-2H-pyran-2-yl)ethyl]-1H-pyrrole-3-carboxamide. Additionally, several of these intermediates may be used as oral prodrugs of the aforementioned hypolipidemic and hypocholesterolemic agents.

SUMMARY OF THE INVENTION

Accordingly, a first aspect of the present invention is a novel process for the preparation of a compound of Formula I

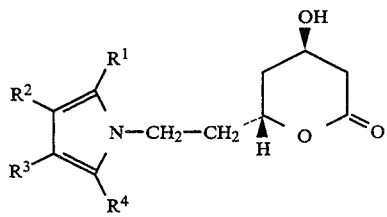

and a dihydroxy acid and pharmaceutically acceptable salts thereof, corresponding to the opened lactone ring of a compound of Formula I
wherein $R^1$ is
1-naphthyl,
2-naphthyl,
cyclohexyl,
cyclohexylmethyl,
norbornenyl,
phenyl,
phenyl substituted with
  fluorine,
  chlorine,
  bromine,
  hydroxyl,
  trifluoromethyl,
  alkyl of from one to four carbon atoms,
  alkoxy of from one to four carbon atoms, or
  alkanoyloxy of from two to eight carbon atoms,
benzyl,
2-,3-, or 4-pyridinyl, or
2-, 3-, or 4-pyridinyl-N-oxide;
$R^2$ or $R^3$ is independently
hydrogen,
alkyl of from one to six carbon atoms,
cyclopropyl,
cyclobutyl,
cyclopentyl,
cyclohexyl,
phenyl,
phenyl substituted with
  fluorine,
  chlorine,
  bromine,
  hydroxyl,
  trifluoromethyl,
  alkyl of from one to four carbon atoms, or
  alkoxy of from one to four carbon atoms, cyano,
  trifluoromethyl, or —$CONR^5R^6$ where $R^5$ and $R^6$ are independently
  hydrogen,
  alkyl of from one to six carbon atoms,
  phenyl,
  phenyl substituted with
    fluorine,
    chlorine,
    bromine,
    cyano, or
    trifluoromethyl;
$R^4$ is
alkyl of from one to six carbon atoms,
cyclopropyl,
cyclobutyl,
cyclopentyl,
cyclohexyl, or
trifluoromethyl;
which comprises:
(a) reacting a compound of Formula XI

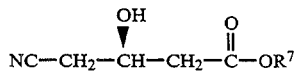

wherein $R^7$ is alkyl of from one to ten carbon atoms with a compound of Formula X

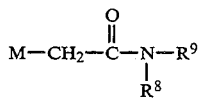

wherein $R^8$ or $R^9$ is independently
alkyl of from one to ten carbon atoms,
cyclopropyl,
cyclobutyl,
cyclopentyl,
cyclohexyl,
benzyl or
phenyl or
$R^8$ and $R^9$ together are
—$(CH_2)_4$—,
—$(CH_2)_5$—,
—$(CH(R^{10}))$—$CH_2)_3$—,
—$(CH(R^{10}))$—$CH_2)_4$—,
—$(CH(R^{10}))$—$(CH_2)_2$—$CH(R^{10}).)$—,
—$(CH(R^{10}))$—$(CH_2)_3$—$CH(R^{10}))$ —,
—$CH_2$—$CH_2$—O—$CH_2$—$CH_2$—,
—$CH(R^{10})$—$CH_2$—O—$CH_2$—$CH_2$—,
—$CH(R^{10})$—$CH_2$—O—$CH_2$—$CH(R^{10})$—,
wherein $R^{10}$ is alkyl of from one to four carbon atoms provided $R^8$ and $R^9$ are not both methyl; and M is zinc, magnesium, sodium, or lithium in a solvent to afford a compound of Formula IX

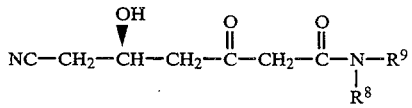

wherein $R^8$ and $R^9$ are as defined above;
(b) reacting a compound of Formula IX with either a compound of formula

wherein $R^{10}$ is as defined above or

wherein R¹⁰ is as defined above followed by NaBH₄ in a solvent to afford a compound of Formula VIII

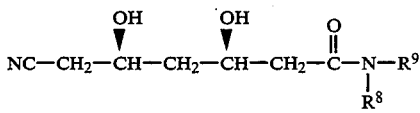

wherein R⁸ and R⁹ are as defined above;

(c) reacting a compound of Formula VIII with a ketal-forming reagent of Formula VII or Formula VIIa

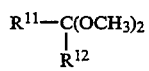

or

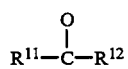

wherein R¹¹ or R¹² is independently alkyl of from one to three carbon atoms or phenyl, or R¹¹ and R¹² are taken together as —(CH₂)ₙ—
wherein n is 4 or 5 in the presence of an acid to afford a compound of Formula VI

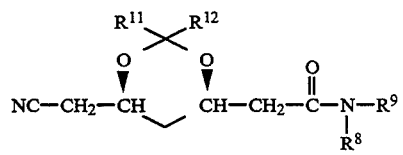

wherein R⁸, R⁹, R¹¹, and R¹² are as defined above;

(d) reacting a compound of Formula VI with hydrogen in the presence of a catalyst and a solvent to afford a compound of Formula V

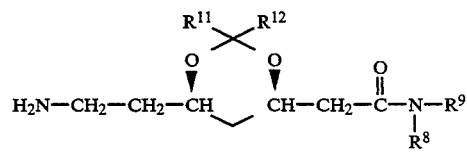

wherein R⁸, R⁹, R¹¹, and R¹² are as defined above;

(e) reacting a compound of Formula V with a compound of Formula IV

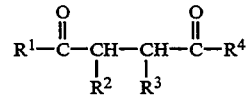

wherein R¹, R², R³, and R⁴ are as defined above in a solvent to afford a compound of Formula III

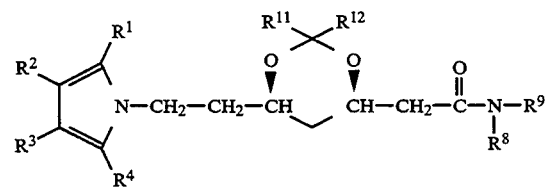

wherein R¹, R² R³, R⁴, R⁸, R⁹, R¹¹, and R¹² are as defined above;

(f) reacting a compound of Formula III with an acid in a solvent to afford a compound of Formula II

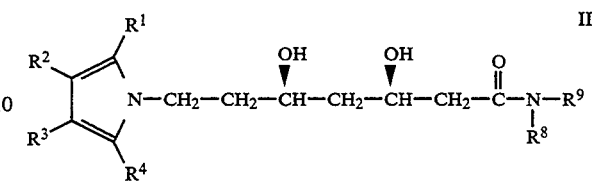

wherein R¹, R², R³, R⁴, R⁸, and R⁹ are as defined above;

(g) (1) hydrolyzing a compound of Formula II with a base, (2) followed by neutralization with an acid, and (3) dissolution and/or heating in a solvent with concomitant removal of water to afford a compound of Formula I;

(h) and if desired converting the resulting compound of Formula I to a dihydroxy acid corresponding to the opened lactone ring of structural Formula I by conventional hydrolysis and further, if desired converting the dihydroxy acid to a corresponding pharmaceutically acceptable salt by conventional means, and if so desired converting the corresponding pharmaceutically acceptable salt to a dihydroxy acid by conventional means, and if so desired converting the dihydroxy acid to a compound of Formula I by dissolution and/or heating in an inert solvent.

A second aspect of the present invention is a novel process for the preparation of the compound of Formula I-1

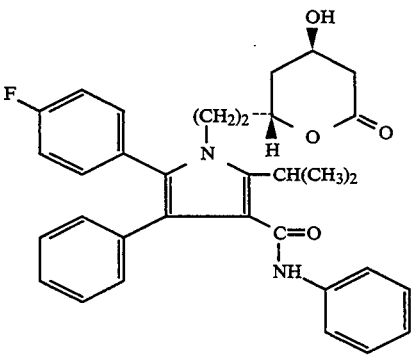

and the dihydroxy acid and pharmaceutically acceptable salts thereof, corresponding to the opened lactone ring of the compound of Formula I-1 which comprises:

(a) reacting the compound of Formula IVa

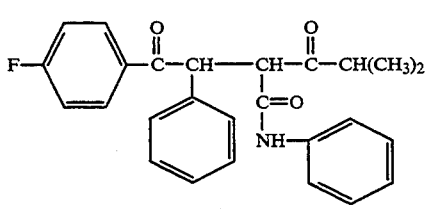

with a compound of Formula V

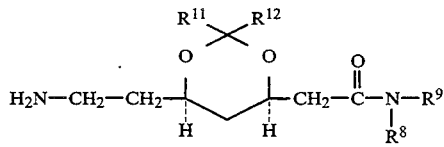

wherein $R^8$ or $R^9$ is independently
alkyl of from one to ten carbon atoms,
cyclopropyl,
cyclobutyl,
cyclopentyl,
cyclohexyl,
benzyl, or
phenyl or
$R^8$ and $R^9$ together are
—$(CH_2)_4$—,
—$(CH_2)_5$—,
—$(CH(R^{10}))$—$(CH_2)_3$—,
—$(CH(R^{10}))$—$(CH_2)_4$—, —$(CH(R^{10}))$—$(CH_2)_2$—$CH(R^{10})$—,
—$(CH(R^{10}))$—$(CH_2)_3$—$CH(R^{10})$—,
—$CH_2$—$CH_2$—$O$—$CH_2$—$CH_2$—,
—$CH(R^{10})$—$CH_2$—$O$—$CH_2$—$CH_2$—,
—$CH(R^{10})$—$CH_2$—$O$—$CH_2$—$CH(R^{10})$—,
wherein $R^{10}$ is alkyl of from one to four carbon atoms provided $R^8$ and $R^9$ are not both methyl; and
$R^{11}$ or $R^{12}$ is independently alkyl of from one to three carbon atoms or phenyl, or
$R^{11}$ and $R^{12}$ are taken together as —$(CH_2)_n$— wherein n is 4 or 5 in a solvent to afford a compound of Formula IIIa

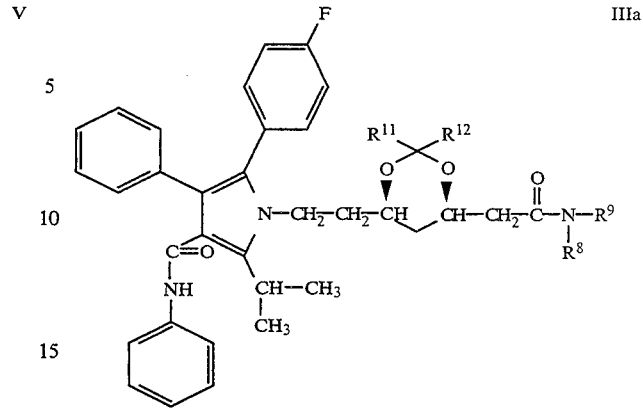

wherein $R^8$, $R^9$, $R^{11}$, and $R^{12}$ are as defined above;
(b) reacting a compound of Formula IIIa with an acid in a solvent to afford a compound of Formula IIa

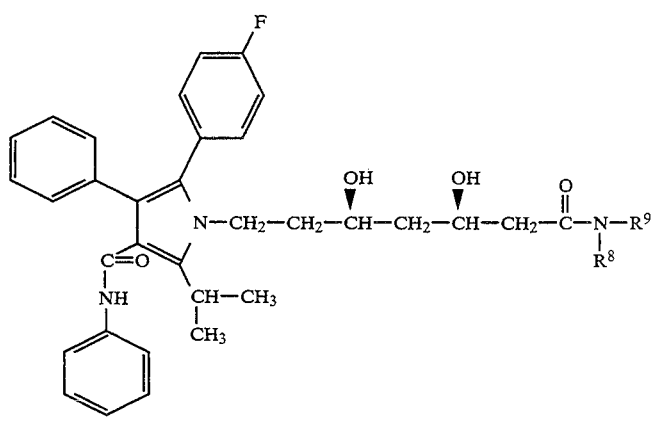

wherein $R^8$ and $R^9$ are as defined above;
(c) (1) hydrolyzing a compound of Formula IIa with a base, (2) followed by neutralization with an acid, and (3) dissolution and/or heating in a solvent with concomitant removal of water to afford a compound of Formula I-1;
(d) and if desired converting the resulting compound of Formula I-1 to a dihydroxy acid corresponding to the opened lactone ring of structural Formula I-1 by conventional hydrolysis and further, if desired converting the dihydroxy acid to a corresponding pharmaceutically acceptable salt by conventional means, and if so desired converting the corresponding pharmaceutically acceptable salt to a dihydroxy acid by conventional means, and if so desired converting the dihydroxy acid to a compound of Formula I-1 by dissolution and/or heating in an inert solvent.

A third aspect of the present invention is a novel intermediate of Formula II

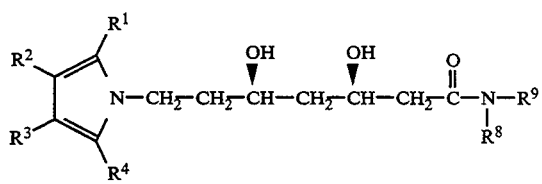

II wherein $R^1$, $R^2$, $R^3$, $R^4$, $R^8$, and $R^9$ are as defined above, which is useful in the preparation of inhibitors of cholesterol biosynthesis of Formula I.

A fourth aspect of the present invention is a novel intermediate of Formula III

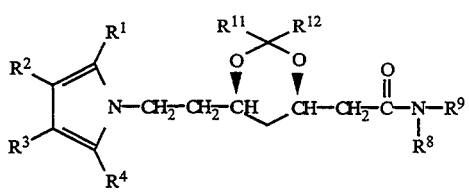

III wherein $R^1$, $R^2$, $R^3$, $R^4$, $R^8$, $R^9$, $R^{11}$, and $R^{12}$ are as defined above, which useful in the preparation of a compound of Formula II, which in turn is useful in the preparation of inhibitors of cholesterol biosynthesis of Formula I.

A fifth aspect of the present invention is a novel intermediate of Formula V

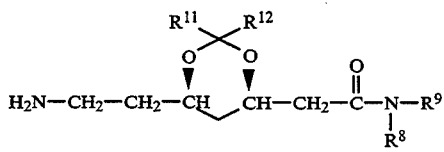

V wherein $R^8$, $R^9$, $R^{11}$, and $R^{12}$ are as defined above, which is useful in the preparation of a compound of Formula III, which in turn is useful in the preparation of a compound of Formula II, which in turn is useful in the preparation of inhibitors of cholesterol biosynthesis of Formula I.

A sixth aspect of the present invention is a novel intermediate of Formula VI

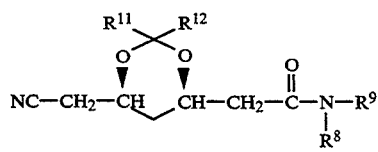

VI wherein $R^8$, $R^9$, $R^{11}$, and $R^{12}$ are as defined above, which is useful in the preparation of a compound of Formula V, which in turn is useful in the preparation of a compound of Formula III, which in turn is useful in the preparation of a compound of Formula II, which in turn is useful in the preparation of inhibitors of cholesterol biosynthesis of Formula I.

A seventh aspect of the present invention is a novel intermediate of Formula VIII

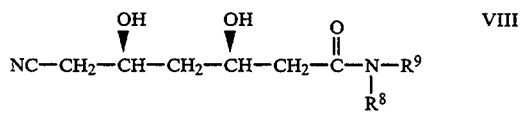

VIII wherein $R^8$ and $R^9$ are as defined above, which is useful in the preparation of a compound of Formula VI, which in turn is useful in the preparation of a compound of Formula V, which in turn is useful in the preparation of a compound of Formula III, which in turn is useful in the preparation of a compound of Formula II, which in turn is useful in the preparation of inhibitors of cholesterol biosynthesis of Formula I.

An eighth aspect of the present invention is a novel intermediate of Formula IX

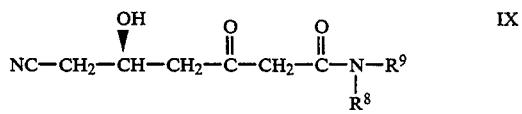

IX wherein $R^8$ and $R^9$ are as defined above, which is useful in the preparation of a compound of Formula VIII, which in turn is useful in the preparation of a compound of Formula VI, which in turn is useful in the preparation of a compound of Formula V, which in turn is useful in the preparation of a compound of Formula III, which in turn is useful in the preparation of a compound of Formula II, which in turn is useful in the preparation of inhibitors of cholesterol biosynthesis of Formula I.

Additionally, it has been found that the novel intermediates of Formula II and Formula III may be used as prodrugs which can be bioconverted following oral administration to the hypolipidemic and hypocholesterolemic agents disclosed in U.S. Pat. Nos. 4,647,576 and 4,681,893.

Thus, a ninth aspect of the present invention is a pharmaceutical composition for administering an effective amount of a compound of Formula II in unit dosage form in the treatment methods mentioned above.

A tenth aspect of the present invention is a pharmaceutical composition for administering an effective amount of a compound of Formula III in unit dosage form in the treatment methods mentioned above.

DETAILED DESCRIPTION OF THE INVENTION

In this invention, the term "alkyl" means a straight or branched hydrocarbon group having from one to ten carbon atoms and includes, for example, methyl, ethyl, n-propyl, isopropyl, n-butyl, isobutyl, tertiary-butyl(1,1-dimethylethyl), n-pentyl, tertiaryamyl, n-hexyl, n-heptyl, n-octyl, n-nonyl, n-decyl, and the like.

"Cycloalkyl" refers to a three- to six-membered saturated hydrocarbon ring and includes, for example, cyclobutyl, cyclopentyl, cyclohexyl, and the like.

"Alkoxy" is O-alkyl in which alkyl is as defined above.

"Alkanoyloxy" is an alkyl group, as defined above, attached to a carbonyl group and thence, through an oxygen atom, to the parent molecular residue.

"Carboalkoxy" is an alkyl group, as defined above, attached to an oxygen atom and thence, through a carbonyl group, to the parent molecular residue.

"Norbornenyl" is a group derived by the removal of a hydrogen atom (other than at a bridgehead carbon atom) from bicyclo[2.2.1]hept-2-ene.

"Benzyl" is also known as phenylmethyl.

"Halogen" is iodine, bromine, and chlorine.

"Alkali metal" is a metal in Group IA of the periodic table and includes, for example, lithium, sodium, potassium, and the like.

"Alkaline-earth metal" is a metal in Group IIA of the periodic table and includes, for example, calcium, barium, strontium, and the like.

"Noble metal" is platinum, palladium, rhodium, ruthenium, and the like.

A preferred compound of Formula I prepared by the improved process of the present invention is one wherein $R^1$ is 1-naphthyl, norbornenyl, phenyl, or
phenyl substituted with fluorine,
chlorine,
bromine,
hydroxyl,
trifluoromethyl,
alkyl of from one to four carbon atoms,
alkoxy of from one to four carbon atoms, or
alkanoyloxy of from two to eight carbon atoms.

Also preferred is a compound of Formula I prepared by the improved process of the present invention wherein $R^4$ is alkyl of from one to six carbon atoms, cyclopropyl, or trifluoromethyl.

Particularly preferred compounds of Formula I prepared by the improved process of the present invention are the following: trans-6-[2-[2-(4-fluorophenyl)-5-(trifluoromethyl)-1H-pyrrol-1-yl]ethyl]tetrahydro-4-hydroxy-2H-pyran-2-one;

trans-6[2-[2-(4- fluorophenyl)-5-methyl- 1H-pyrrol-1-yl]ethyl]tetrahydro-4-hydroxy-2H-pyran-2- one;

trans-6-[2-[2-(4-fluorophenyl)-5-(1-methylethyl)-1H-pyrrol-1-yl]ethyl]tetrahydro-4-hydroxy- 2H-pyran-2-one;

trans-6-[2-[2-cyclopropyl-5-(4-fluorophenyl)1H-pyrrol-1-yl]ethyl]tetrahydro-4-hydroxy-2H-pyran-2-one;

trans-6-[2-[2-(1,1-dimethylethyl)-5-(4-fluorophenyl)-1H-pyrrol-1- yl]ethyl]tetrahydro-4- hydroxy-2H-pyran-2-one;

trans-tetrahydro-4-hydroxy-6-[2-[2-(2-methoxyphenyl)-5-methyl-1H-pyrrol-1-yl]ethyl]-2H-2-one;

trans-tetrahydro-4-hydroxy-6-[2-[2-(2-methoxyphenyl)-5- (1-methylethyl)-1H-pyrrol-1-yl]ethyl]-2H-pyran-2-one;

trans-tetrahydro-4-hydroxy-6-[2-[2-methyl-5-(1-naphthalenyl)-1H-pyrrol-1-yl]ethyl]-2H-pyran-2-one;

trans-6-[2-(2-bicyclo[2.2.1]hept-5-en-2-yl-5-methyl -1H-pyrrol-1- yl)ethyl]tetrahydro-4-hydroxy-2H-pyran-2-one;

trans (±)-5-(4-fluorophenyl)-2- (1-methylethyl)-N,4-diphenyl-1-[2-(tetrahydro-4-hydroxy-6-oxo-2H-pyran-2-yl)ethyl]-1H-pyrrole-3-carboxamide;

(2R) - trans)-5-(4-fluorophenyl)-2-(1-methylethyl)N,4-diphenyl -1-[2-(tetrahydro-4-hydroxy-6-oxo-2H-pyran-2-yl)ethyl]-1H-pyrrole-3-carboxamide;

trans-2-(4-fluorophenyl)-N,4-diphenyl-1-[2-(tetrahydro-4-hydroxy-6-oxo-2H-pyran-2-yl)ethyl]-5-trifluoromethyl-1H-pyrrole-3-carboxamide;

trans-5-(4-fluorophenyl)-N,4-diphenyl-1- [2-(tetrahydro-4-hydroxy-6-oxo-2H-pyran-2-yl)ethyl]-2-trifluoromethyl-1H-pyrrole-3-carboxamide; and a dihydroxy acid and pharmaceutically acceptable salts thereof, corresponding to the opened lactone ring of compounds of structural Formula I.

As previously described, the compounds of Formula I are useful as inhibitors of the enzyme 3-hydroxy- 3-methylglutaryl-coenzyme A reductase (HMG CoA reductase) and are thus useful as hypolipidemic or hypocholesterolemic agents.

The ability of a compound of Formula II or Formula III to act as a prodrug of the hypolipidemic and hypocholesterolemic agents disclosed in U.S. Pat. Nos. 4,647,576 and 4,681,893 may be demonstrated in a standard in vivo pharmacological assay in dogs as disclosed in European Published Patent Application 0259068-A2.

The process of the present invention in its first aspect is a new, improved, economical, and commercially feasible method for preparing HMG CoA reductase inhibitors of Formula I. The process of the present invention in its first aspect is outlined in Scheme I.

SCHEME I $$NC-CH_2-\overset{OH}{\underset{\blacktriangledown}{CH}}-CH_2-\overset{O}{\overset{\|}{C}}-OR^7 + M-CH_2-\overset{O}{\overset{\|}{C}}-\underset{R^8}{N}-R^9 \longrightarrow NC-CH_2-\overset{OH}{\underset{\blacktriangledown}{CH}}-CH_2-\overset{O}{\overset{\|}{C}}-CH_2-\overset{O}{\overset{\|}{C}}-\underset{R^8}{N}-R^9$$

XI        X        IX

1) $R_2{}^{10}BOCH_3$ or $R_3{}^{10}B$
2) $NaBH_4$ $$NC-CH_2-\overset{OH}{\underset{\blacktriangledown}{CH}}-CH_2-\overset{OH}{\underset{\blacktriangledown}{CH}}-CH_2-\overset{O}{\overset{\|}{C}}-\underset{R^8}{N}-R^9$$

VIII $R^{11}-C(OCH_3)_2$
$\underset{R^{12}}{|}$   or   $R^{11}-\overset{O}{\overset{\|}{C}}-R^{12}$ VII            VIIa

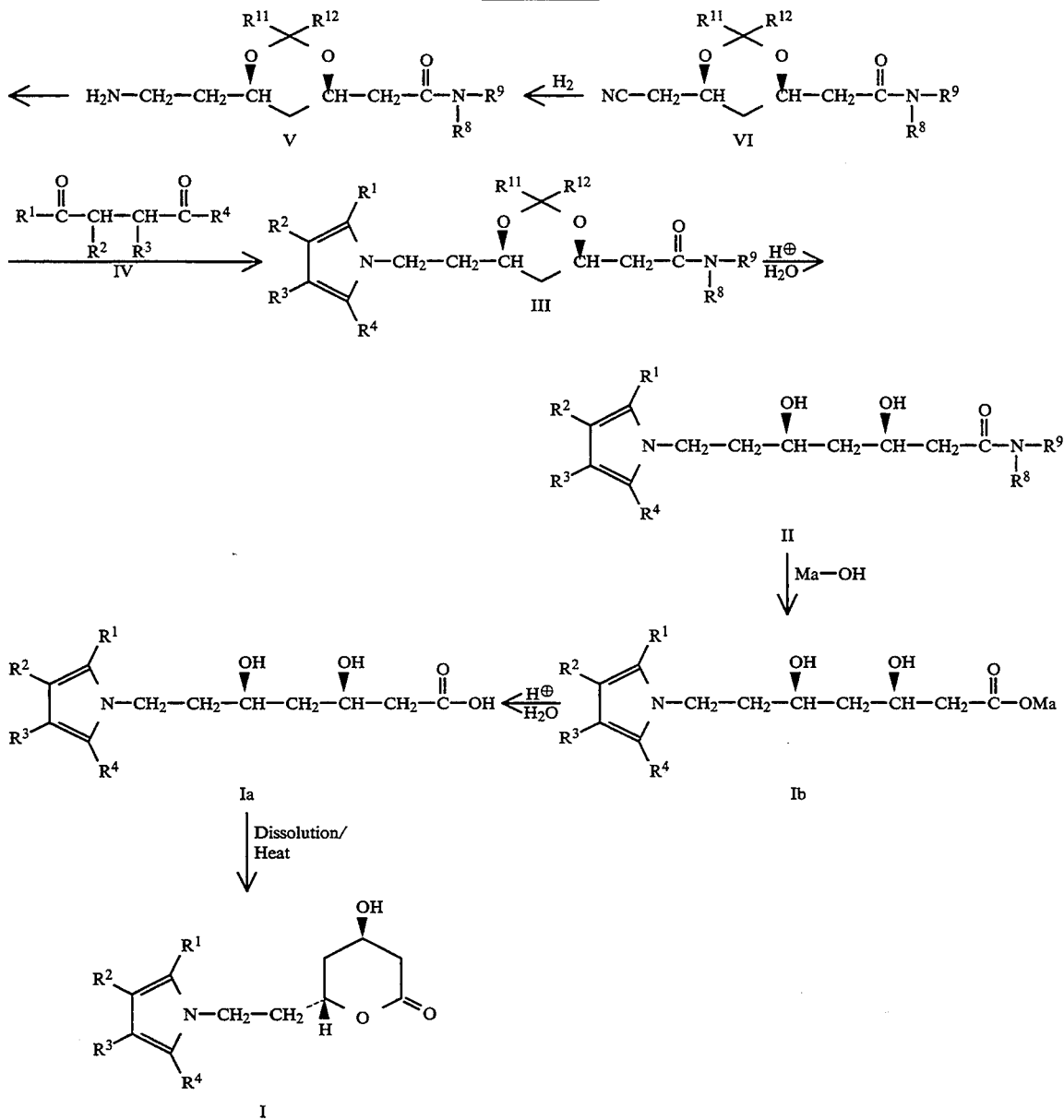

Thus, the (R) -5-cyano-3-hydroxybutyric acid ester of Formula XI wherein $R^7$ is alkyl of from one to ten carbon atoms is treated with an α-metal amide of Formula X.

wherein $R^8$ or $R^9$ is independently
  alkyl of from one to ten carbon atoms,
  cyclopropyl,
  cyclobutyl,
  cyclopentyl,
  cyclohexyl,
  benzyl, or
  phenyl or
$R^8$ and $R^9$ together are
  —(CH$_2$)$_4$—,
  —(CH$_2$)$_5$—,
  —(CH(R$^{10}$)—CH$_2$)$_3$—,
  —(CH(R$^{10}$)—CH$_2$)$_4$—,
  —(CH(R$^{10}$)—(CH$_2$)$_2$—CH(R$^{10}$))—,
  —(CH(R$^{10}$)—(CH$_2$)$_3$—CH(R$^{10}$))—,
  —CH$_2$—CH$_2$—O—CH$_2$—CH$_2$—,
  —CH(R$^{10}$)—CH$_2$—O—CH$_2$—CH$_2$—,
  —CH(R$^{10}$)—CH$_2$—O—CH$_2$—CH(R$^{10}$)—,
wherein $R^{10}$ is alkyl of from one to four carbon atoms provided $R^8$ and $R^9$ are not both methyl and M is zinc, magnesium, sodium, or lithium at about 0° C. to about −40° C. in a solvent, such as, for example, a mixture of tetrahydrofuran/heptane, and the like for about 30 minutes and subsequently poured into a solution of an acid, such as, for example, 2.2N hydrochloride acid to afford a compound of Formula IX wherein $R^8$ and $R^9$ are as defined above. Preferably, the reaction is carried out at about 0° C. to about −20° C. in a mixture of tetrahydrofuran/heptane for about 30 minutes and subsequently poured into 2.2N hydrochloric acid.

A hydroxy ketone amide of Formula IX is treated with a borane reagent, such as, for example, a compound of formula

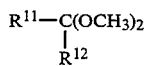

wherein $R^{10}$ is lower alkyl, for example, tributylborane in the presence of air or a compound of formula

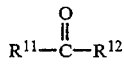

wherein $R^{10}$ is as defined above, for example, methoxydiethylborane in the absence of air and subsequent treatment with a metal hydride, such as, for example, sodium borohydride in a solvent, such as, for example, methanol, tetrahydrofuran, mixtures thereof, and the like at about 0° C. to about $-110°$ C. for about 5 hours followed by subsequent treatment with an acid, such as, for example, glacial acetic acid, and the like to afford a compound of Formula VIII wherein $R^8$ and $R^9$ are as defined above. Preferably, the reaction is carried out with methoxydiethylborane under a nitrogen atmosphere and subsequent treatment with sodium borohydride in a mixture of methanol and tetrahydrofuran at about $-20°$ C. to about $-78°$ C. for about 5 hours followed by the addition of glacial acetic acid.

A 3,5-dihydroxy amide of Formula VIII is treated with a ketal-forming reagent of Formula VII or Formula VIIa $$R^{11}-\underset{\underset{R^{12}}{|}}{C}(OCH_3)_2 \qquad \text{VII}$$

or $$R^{11}-\overset{\overset{O}{\|}}{C}-R^{12} \qquad \text{VIIa}$$

wherein $R^{11}$ or $R^{12}$ is independently
 alkyl of from one to three carbon atoms or
 phenyl or
$R^{11}$ and $R^{12}$ are taken together as $-(CH_2)_n-$ wherein n is 4 or 5, for example, a ketal-forming reagent selected from the group consisting of acetone, 2,2-dimethoxypropane, 2-methoxypropene, cyclopentanone, cyclohexanone, 1,1-dimethoxycyclopentane, 1,1-dimethoxycyclohexane, and the like or optionally an acetal forming reagent, for example, benzaldehyde, and the like in the presence of an acid, such as, for example, methanesulfonic acid, camphorsulfonic acid, paratoluenesulfonic acid, and the like, in the presence of excess reagent or in an inert solvent, such as, for example, dichloromethane, and the like at about 0° C. to about the reflux temperature of the reagent or solvent to afford a compound of Formula VI wherein $R^8$, $R^9$, $R^{11}$, and $R^{12}$ are as defined above. Preferably, the reaction is carried out with a ketone forming reagent of Formula VII, for example, 2,2-dimethoxypropane and acetone in the presence of methanesulfonic acid at about room temperature.

A compound of Formula VI is treated with hydrogen gas in an alcohol, such as, for example methanol saturated with anhydrous ammonia or aqueous ammonium hydroxide, and the like, in the presence of a catalyst, such as, for example, Raney nickel, Raney cobalt, a noble metal catalyst, such as, for example, platinum oxide in the presence of an alkanoic acid, such as acetic acid, and the like to afford a compound of Formula V wherein $R^8$, $R^9$, $R^{11}$, and $R^{12}$ are as defined above. Preferably, the reaction is carried out with hydrogen gas in the presence of Raney nickel in methanol saturated with anhydrous ammonia.

A compound of Formula V is reacted with a diketone of Formula IV
wherein $R^1$ is
 1-naphthyl,
 2-naphthyl,
 cyclohexyl,
 cyclohexylmethyl,
 norbornenyl,
 phenyl,
 phenyl substituted with
  fluorine,
  chlorine,
  bromine,
  hydroxyl,
  trifluoromethyl,
  alkyl of from one to four carbon atoms,
  alkoxy of from one to four carbon atoms, or
  alkanoyloxy of from two to eight carbon atoms,
 benzyl,
 2-, 3-, or 4-pyridinyl, or
 2-, 3-, or 4-pyridinyl-N-oxide;
$R^2$ or $R^3$ is independently
 hydrogen,
 alkyl of from one to six carbon atoms,
 cyclopropyl,
 cyclobutyl,
 cyclopentyl,
 cyclohexyl,
 phenyl,
 phenyl substituted with
  fluorine,
  chlorine,
  bromine,
  hydroxyl,
  trifluoromethyl,
  alkyl of from one to four carbon atoms, or
  alkoxy of from one to four carbon atoms,
 cyano,
 trifluoromethyl, or $-CONR^5R^6$ where $R^5$ and $R^6$ are
  independently
  hydrogen,
  alkyl of from one to six carbon atoms,
  phenyl,
  phenyl substituted with
   fluorine,
   chlorine,
   bromine,
   cyano, or
   trifluoromethyl;
$R^4$ is
 alkyl of from one to six carbon atoms,
 cyclopropyl,
 cyclobutyl,
 cyclopentyl,
 cyclohexyl, or
 trifluoromethyl; in an inert solvent or mixtures thereof, such as, for example, tetrahydrofuran, heptane, toluene, and the like at about the reflux temperature of the solvent in the presence of a catalyst of formula $$R^{13}CO_2H$$

wherein $R^{13}$ is $CH_3-$, $CF_3-$, $Cl-CH_2-$, $Cl-CH_2-CH_2-$, $C_6H_5-CH_2-CH_2$, $C_6H_5-CH_2-$, $HO_2C-CH_2-$, $HO_2C-CH_2-CH_2-$, $C_6H_5-$, para- Cl—$C_6H_5$—, para —$CH_3$—$C_6H_5$—, meta —$CH_3$—$C_6H_5$—, tertiary-$C_4H_9$—, or triethylamine hydrochloride to give a compound of Formula III wherein $R^1$, $R^2$, $R^3$, $R^4$, $R^8$, $R^9$, $R^{11}$, and $R^{12}$ are as defined above. Preferably, the reaction is carried out in heptane/tetrahydrofuran/toluene in the presence of pivalic acid at about the reflux temperature of the solvent mixture.

A compound of Formula III, a hydroxy-protected pyrrole amide, is treated with an acid, such as, for example, aqueous hydrochloric acid, and the like in an inert solvent, such as, for example, tetrahydrofuran, methanol, and the like to afford a compound of Formula II wherein $R^1$, $R^2$, $R^3$, $R^4$, $R^7$, $R^8$, and $R^9$ are as defined above. Preferably, the reaction is carried out in methanol in the presence of 1.0N hydrochloric acid solution.

A compound of Formula II, the beta, gamma-dihydroxy-pyrroleheptaneamide, is hydrolyzed with a base, such as, for example, alkali metal hydroxide, for example, sodium hydroxide or an alkaline-earth metal hydroxide in a solvent, such as, for example methanol, and the like and subsequent washing with an inert solvent, such as, for example, toluene, methyl tertbutyl methyl ether, and the like to afford a compound of Formula Ib wherein M is lithium, sodium, potassium, calcium, barium, strontium, and the like and $R^1$, $R^2$, $R^3$, and $R^4$ are as defined above. Preferably, the reaction is carried out in methanol with 2.0 N aqueous sodium hydroxide and subsequent washing with tert-butyl methyl ether.

Optionally, a compound of Formula Ib wherein Ma is sodium and $R^1$, $R^2$, $R^3$, and $R^4$ are as defined above may be converted to a hemi-calcium salt compound of Formula Ib by treatment with an aqueous solution of calcium acetate.

A compound of Formula Ib is treated with an acid, such as, for example, dilute aqueous hydrochloric acid and subsequently extracted into an inert solvent, such as, for example, tert-butyl methyl ether, diethyl ether, hexane, toluene, and the like to afford a compound of Formula Ia wherein $R^1$, $R^2$, $R^3$, and $R^4$ are as defined above. Preferably, the reaction is carried out with 2N aqueous hydrochloric acid and subsequent extraction into tert-butyl methyl ether.

A compound of Formula Ia is dissolved and/or heated in an inert solvent, such as, for example, toluene, and the like, with or without concomitant removal of water to afford a compound of Formula I, wherein $R^1$, $R^2$, $R^3$, and $R^4$ are as defined above. Preferably, the reaction is carried out by dissolving and/or heating a compound of Formula Ia in toluene at about reflux with azeotropic removal of water.

The process of the present invention in its second aspect is a new, improved, economical, and commercially feasible method for preparing the HMG CoA reductase inhibitor of Formula Ic. The process of the present invention in its second aspect is outlined in Scheme II.

SCHEME II

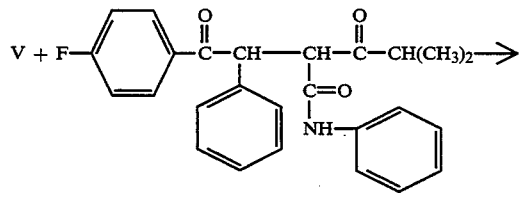

IVa

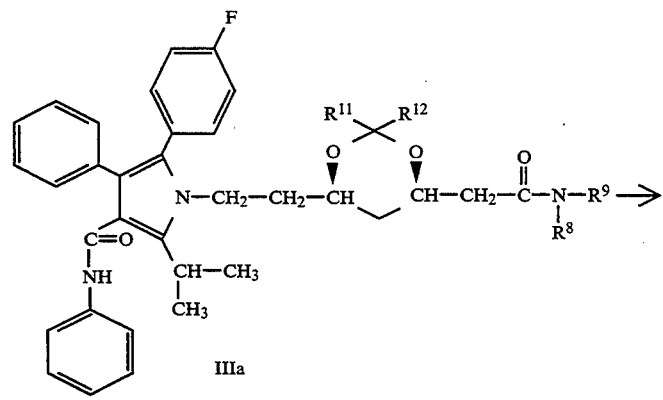

IIIa

SCHEME II

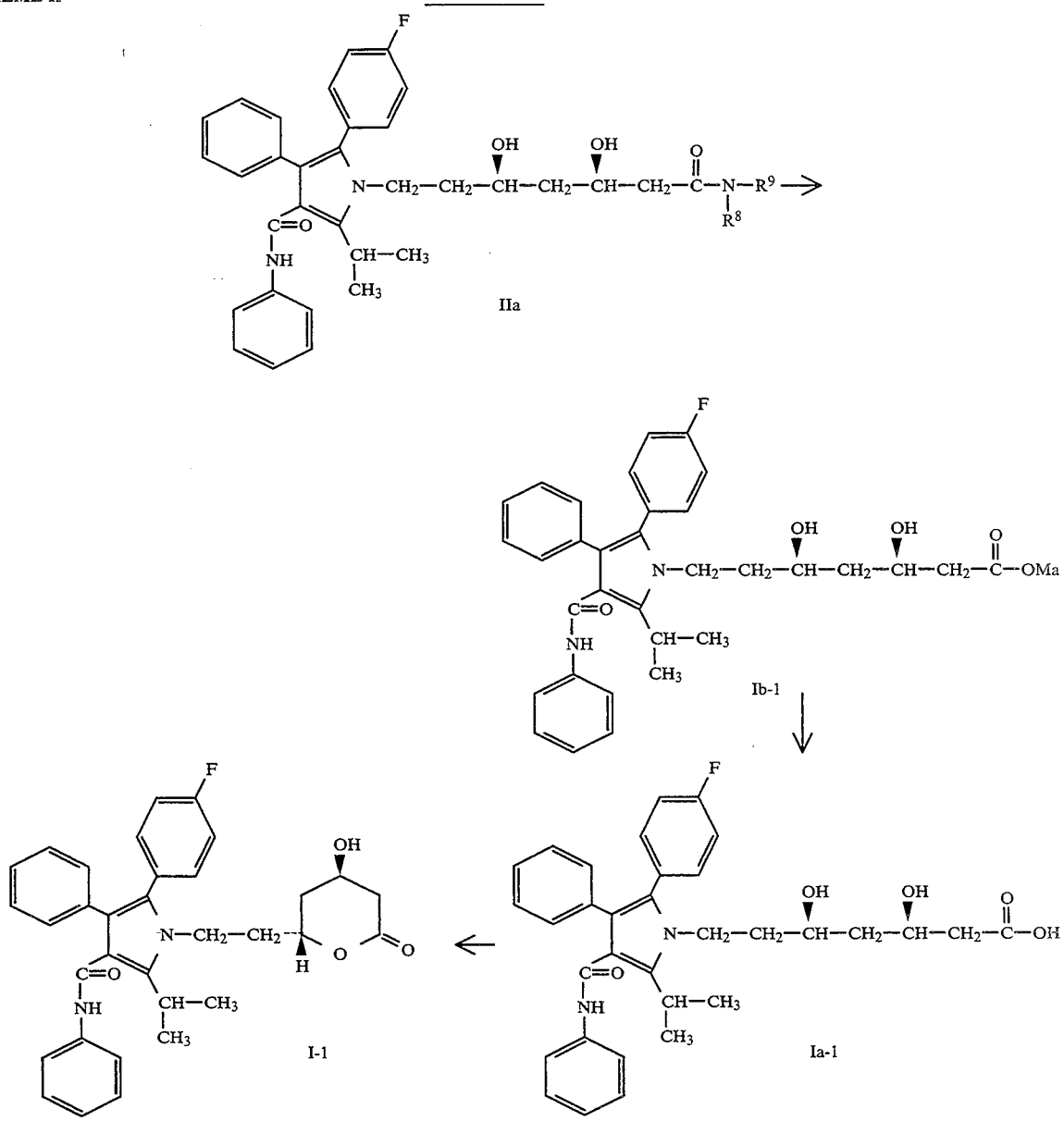

Thus, a compound of Formula V is reacted with the compound of Formula IVa using the methodology used to prepare a compound of Formula III from a compound of Formula V and a compound of Formula IV to afford a compound of Formula IIIa wherein $R^8$, $R^9$, $R^{11}$, and $R^{12}$ are as defined above.

A compound of Formula IIIa is converted to a compound of Formula IIa wherein $R^8$, $R^9$, and M are as defined above using the methodology used to prepare a compound of Formula II from a compound of Formula III.

A compound of Formula IIa is converted to a compound of Formula Ib-1 wherein M is as defined above using the methodology used to prepare a compound of Formula Ib from a compound of Formula II.

A compound of Formula Ib-1 is converted to a compound of Formula Ia-1 using the methodology used to prepare a compound of Formula Ia from a compound of Formula Ib.

A compound of Formula Ia-1 is converted to a compound of Formula I-1 using the methodology used to prepare a compound of Formula I from a compound of Formula Ia.

The optically active 3 (R) centers in compounds of Formula XI establishes the optically active center or centers desired in Formula Ix, Formula VIII, Formula VI, Formula V, Formula III, Formula IIIa, Formula II, Formula IIa, Formula Ib, Formula Ib-1, Formula Ia, Formula Ia-1, Formula I, and Formula I - 1.

Compounds of Formula XI, Formula VII, Formula IV, Formula IVa, are either known or capable of being prepared by methods known in the art.

The ring-opened dihydroxy acids of Formula Ia and Formula Ia-1 may be prepared from the lactone compounds of Formula I or Formula I-1, respectively, by conventional hydrolysis, such as, for example, sodium hydroxide in methanol, sodium hydroxide in tetrahydrofuran-water, and the like, of the lactone compounds of Formula I or Formula I-1.

In the ring-opened dihydroxy acid form, compounds of the present invention react to form salts with pharmaceutically acceptable metal and amine cations formed from organic and inorganic bases. The term "pharmaceutically acceptable metal salt" contemplates salts formed with the sodium, potassium, calcium, magnesium, aluminum, iron, and zinc ions. The term "pharmaceutically acceptable amine salt" contemplates salts with ammonia and organic nitrogenous bases strong enough to form salts with carboxylic acids. Bases useful for the formation of pharmaceutically acceptable nontoxic base addition salts of the compound of the present invention form a class whose limits are readily understood by those skilled in the art.

The dihydroxy free acid form of the compounds of the invention may be regenerated from the salt form, if desired, by contacting the salt with a dilute aqueous solution of an acid, such as hydrochloric acid.

The ring closed lactone form of the compounds of the invention may be regenerated by dissolution of the dihydroxy free acid form of the compounds of the invention in an inert solvent such as, for example, toluene, benzene, ethyl acetate, and the like, at about 0° C. to about the boiling point of the solvent usually but not necessarily with concomitant removal of the resulting water and usually but not necessarily with strong acid catalysis such as, for example, concentrated hydrochloric acid and the like.

The base addition salts may differ from the free acid forms of the compounds of this invention in such physical characteristics as solubility and melting point, but are otherwise considered equivalent to the free acid form for the purposes of this invention.

The compounds of the present invention may exist in solvated or unsolvated form and such forms are equivalent to the unsolvated form for the purposes of this invention.

The compounds of structural Formulas I, and I-1, above possess two asymmetric carbon centers, one at the 4-hydroxy position of the pyran-2-one ring, and the other at the 6-position of the pyran-2-one ring where the alkylpyrrole group is attached. This asymmetry gives rise to four possible isomers, two of which are the 4R,6S and 4S,6R-isomers and the other two of which are the 4R,6R and the 4S,6S-isomers. The preferred isomer in this invention is the 4R,6R-isomer of the compounds of Formulas I, and I-1, above.

The compounds of Formula II or Formula III of the present invention can be prepared and administered in a wide variety of oral forms.

For preparing pharmaceutical compositions from the compounds of the present invention, pharmaceutically acceptable carriers can be either solid or liquid. Solid form preparations include powders, tablets, pills, capsules, cachets, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from 5% or 10% to about 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

Liquid form preparations include solutions, suspensions, and emulsions, for example, water or water propylene glycol solutions.

Aqueous solutions suitable for oral use can be prepared by dissolving the active component in water and adding suitable colorants, flavors, stabilizing, and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials. Also, the unit dosage form can be a capsule, tablet, cachet, or lozenge itself, or it can be the appropriate number of any of these in packaged form.

The quantity of active component in a unit dose preparation may be varied or adjusted from 2.5 mg to 2000 mg preferably 5 mg to 600 mg according to the particular application and the potency of the active component. The composition can, if desired, also contain other compatible therapeutic agents.

In therapeutic use as hypolipidemic and hypocholesterolemic agents, the compounds of Formula II or Formula III utilized in the pharmaceutical method of this invention are administered at the initial dosage of about 0.01 mg to about 8 mg/kg daily. A daily dose range of about 0.01 mg to about 10 mg/kg is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

The following nonlimiting examples illustrates the inventors' preferred method for preparing the compounds of the invention.

EXAMPLE 1

[R-(R*,R*)]-2-(4-Fluorophenyl)-β,δ-dihydroxy-5-(1-methylethyl)-3-phenyl-4-[(phenylamino)carbonyl]-1H-pyrrole-1-heptanoic acid, hemi calcium salt

Step 1: Preparation of (R)-6-cyano-5-hydroxy-3-oxo-N,N-diphenylhexanamide

To a stirred −10° C. solution of N,N-diphenylacetamide (211 g, 1.0 mol) in tetrahydrofuran (1.0 L) is slowly added a solution of lithium diisopropylamide in tetrahydrofuran-heptane (0.5 L of 2 M) while maintaining the temperature between −10° C. to −5° C. The mixture is stirred at −0° C. to 20° C. for 30 minutes. (R)-4-cyano-3-hydroxybutyric acid, ethyl ester (Brower, supra) (40 g, 0.25 mol) as a solution in 200 mL of tetrahydrofuran is added to the previously prepared anion. The reaction mixture is stirred for 30 minutes at −5° C. to −20° C., and transferred to a 2.2N aqueous hydrochloric acid solution (1 L). The aqueous layer is extracted with 500 mL of ethyl acetate, the aqueous layer is separated and reextracted with 100 mL of ethyl acetate, the extracts are combined and concentrated in vacuo to afford crude (R)-6-cyano-5-hydroxy-3-oxo-N,N-diphenylhexanamide which is not isolated. A small sample is purified by column chromatography on flash silica gel (60:40 hexane:ethyl acetate) as an oil. Proton nuclear magnetic resonance spectroscopy ($^1$H-NMR): (Acetone-d$_6$) δ 2.02 (m, 2H), 2.73 (m, 2H), 4.1 (m, 2H), 4.52 (m, 1H), 4.74 (s, 1H), 7.2–7.4 (m, 10H). Molecular weight: 322. Gas Chromatography/Mass Spectroscopy (GC/MS) m/e 322, 169, 154, 141, 128, 115, 77, 65, 51, 39, 32.

STEP 2

Preparation of [R-(R*,R*)]-6-cyan0-3,5-dihydroxy-N,N-diphenylhexanamie

Crude (R)-6-cyano-5-hydroxy-3-oxo-N,N-diphenylhexanamide, approximately 0.2 mol, is dissolved in tetrahydrofuran (200 mL) and methanol (100 mL) under a nitrogen atmosphere. The solution is cooled to −20° C., and a 50% solution of methoxydiethylborane in tetrahydrofuran (105 mL) is added. The reaction is cooled to −78° C., and sodium borohydride (24 g, 0.63 mol) is added over 30 minutes. The reaction mixture is maintained at −78° C. for 5 hours, allowed to warm to room temperature, and stand for 10 hours under a nitrogen atmosphere. The reaction is quenched by the addition of acetic acid (40 mL) and concentrated by vacuum distillation to an oil. The residue is dissolved with methanol (400 mL), concentrated by vacuum distillation, redissolved with methanol (300 mL), and reconcentrated by vacuum distillation to give a yellow oil. The oil is taken up in ethyl acetate (300 mL) and washed with deionized water (500 mL). The ethyl acetate solution is concentrated by vacuum distillation to give [R-(R*,R,)]-6-cyano-3,5-dihydroxy-N,N-diphenylhexanamide as an oil which is used without further purification. A small sample is purified by column chromatography on flash silica gel (60:40 hexane:ethyl acetate) as an oil.

$^1$H-NMR:(CDCl$_3$) δ1.6 (m, 2H), 2.4 (m, 2H), 2.5 (m, 2H), 4.1 (m, 1H), 4.2 (m, 1H), 4.4 (s, 1H), 4.8 (s, 1H), 7.1→7.5 (m, 10H). Molecular weight: 324. GC/MS m/e 324, 307, 284, 266, 240, 212, 186, 170, 158, 130, 112.

STEP 3

Preparation of (4R-cis)-6-(cyanomethyl)-2,2-dimethyl-N,N-diphenyl-1,3-dioxane-4-acetamide Crude [R-(R*,R*)]-6-cyano-3,5-dihydroxy-N,N-diphenylhexanamide, approximately 0.18 mol, is dissolved in 2,2-dimethoxypropane (160 mL, 1.5 mol) and acetone (300 mL). Methanesulfonic acid (0.5 mL) is added, and the solution is stirred for 2 hours at room temperature. The reaction is quenched by the addition of aqueous sodium bicarbonate (800 mL) and ethyl acetate (500 mL). The ethyl acetate solution is concentrated by vacuum distillation to give 62.5 g of (4R-cis)-6-(cyanomethyl)-2,2-dimethyl-N,N-diphenyl-1,3-dioxane-4-acetamide as an off-white crystalline solid (mp 98°–100° C., uncorrected).

$^1$H-NMR (CDCl$_3$) δ1.37 (s, 3H), 1.46 (s, 3H), 1.82 (d, 1H, J=13 Hz), 2.33 (dd, 1H, J=16, 6H), 2.48 (d, 1H, J=6 Hz), 2.60 (dd, 1H, J=16, 6 Hz), 4.0–4.2 (m, 2H), 4.4–4.6 (m, 2H), 7.0–7.5 (m, 10H). Molecular weight: 364. GC/MS m/e 364, 349, 307, 289, 196, 169, 154, 138, 93, 77, 59, 43.

STEP 4

Preparation of (4R-cis)-6-(2-aminoethyl)-2,2-dimethyl-N,N-diphenyl-1,3-dioxane-4-acetamide A solution of (4R-cis)-6-(cyanomethyl)-2,2-dimethyl-N,N-diphenyl-1,3-dioxane-4-acetamide (10.0 g, 0.027 mol) in methanol (150 mL) containing anhydrous ammonia (2.25 g) is reacted with hydrogen gas in a Parr shaker at 30° C. in the presence of a slurry of Raney nickel A-7000 (3.8 g). After 3 hours, uptake of hydrogen has ceased, the mixture is cooled to 20° C., the atmosphere is vented and exchanged for nitrogen, the slurry is filtered through celite, and concentrated at reduced pressure to give 9.5 g of (4R-cis)-6-(2-aminoethyl)-2,2-dimethyl-N,N-diphenyl-1,3-dioxane-4-acetamide as an oil.

$^1$H-NMR (DMSO) δ1.23 (S, 3H), 1.37 (S, 3H), 2.29 (m, 1H), 2.33 (m, 1H), 2.36 (m, 2H), 2.49 (m, 2H), 2.50 (m, 2H), 3.01 (m, 2H), 3.22 (s, 2H), 7.37 (s, 10H).

STEP 5

Preparation of (4R-cis)-1-[2-[6-[2-(diphenylamino)-2-oxoethyl]- 2,2 -dimethyl-1,3 -dioxan-4-yl]ethyl]-5-(4- fluorophenyl)- 2-(1-methylethyl)-N,4-diphenyl-1H -pyrrole-3-carboxamide A nitrogen purged 500 mL three-neck flask is charged with 4-fluoro-α-(2-methyl-1-oxopropyl)- γ-oxo-N,β-diphenylbenzenebutanamide (Baumann, supra) (13.6 g, 0.032 mol), (4R-cis)-6-(2-aminoethyl)-2,2-dimethyl-N,N-diphenyl-1,3-dioxane-4-acetamide (10.0 g, 0.027 mol), heptane (100 mL), pivalic acid (3 g), tetrahydrofuran (50 mL), and toluene (60 mL). The mixture is heated to reflux for 48 hours, cooled to room temperature, and diluted with toluene (300 mL). The solution is washed with 0.5N aqueous sodium hydroxide (150 mL), followed by 0.5N aqueous hydrochloric acid (250 mL), and concentrated by vacuum distillation to a foam. The product, (4R-cis)-1-[2-[6-[2-(diphenylamino)-2-oxoethyl]-2,2-dimethyl-1,3-dioxan-4-yl]ethyl]-5-(4-fluorophenyl)-2-(1-methylethyl)-N,4-diphenyl- 1H-pyrrole-3-carboxamide, is used in the next step without further purification. Fourier Transform Infrared Spectroscopy (FTIR)(KBr) 3450, 2860, 1650, 1620 cm$^{-1}$;

$^1$H-NMR (DMSO) δ1.27 (s, 3H), 1.31 (s, 3H), 1.34 (s, 3H), 1.72 (s, 3H), 2.05 (m, 1H), 2.47 (m, 1H), 3.25 (m, 2H), 3.27 (m, 2H), 3.29 (m, 2H), 3.32 (s, 1H), 3.32 (s, 1H), 7.0–7.4 (m, 24H).

STEP 6

Preparation of
[R-(R*,R*)]-5-(4-fluorophenyl)-β-δ-dihydroxy-2-(1-methylethyl)-N,N,4-triphenyl-3-[(phenylamino)carbonyl]-1H-pyrrole-1- heptanamide (4R-cis)-1-[2-[6-[2- (diphenylamino) -2-oxoethyl]-2,2-dimethyl- 1,3 -dioxan-4-yl ]ethyl ]-5-(4- fluorophenyl)-2-(1-methylethyl)- N,4-diphenyl-1H- pyrrole -3-carboxamide is dissolved in methanol (300 mL) and reacted by adding 1.0N hydrochloric acid (100 mL) and stirring for 12 hours at room temperature. The white crystalline solid [R-(R*,R*) ]-5- (4-fluorophenyl)-β,δ-dihydroxy-2-(1-methylethyl)-N,N,4-triphenyl-3-[(phenylamino) carbonyl]-1H-pyrrole- 1-heptanamide is isolated by filtration (mp 228.5°–232.9° C., uncorrected).

FTIR (KBr) 3400 (broad), 2850 1640 cm$^{-1}$; $^1$H-NMR (CDC13) δ1.50 (m, 1H), 1.54 (m, 1H), 1.8–1.95 (s, 6H), 2.0–2.17 (m, 8H), 3.70 (s, 1H), 7.1–7.4 (m, 24H), 11.16 (s, 2H).

STEP 7

Preparation of
[R-(R*,R*)]-2-(4-Fluorophenyl)-β,δ-dihydroxy-5-(1-methylethyl)-3-phenyl-4-[(phenylamino)carbonyl]-1H-pyrrole-1-heptanoic acid, sodium salt A nitrogen purged 500 mL three-neck flask is charged with [R-(R*,R*)]-5-(4-fluorophenyl)-β,δ-dihydro-2-(1-methylethyl)-N,N,4-triphenyl-3-[(phenylamino)carbonyl]-1H-pyrrole-1-heptanamide (4.0 g, methanol (30 mL), and 2.0N aqueous sodium hydroxide (60 mL). The mixture is heated to 70° C. for 4 hours and cooled to room temperature. A white solid is filtered and discarded. The filtrate is washed with tert-butyl methyl ether, and the aqueous layer is acidified to a pH of 2 by the addition of 2N aqueous hydrochloric acid and extracted with tert-butyl methyl ether. The organic layer is separated, mixed with water (200 mL), methanol (20 mL), and brought to a pH of 12 by addition of 2.0N aqueous sodium hydroxide. The aqueous layer is washed with tert-butyl methyl ether (50 mL) and water (100 mL). The aqueous layer contains the sodium salt of [R- (R*,R*) ]-2- (4-fluorophenyl)β,δ-dihydroxy-5-(1-methylethyl )-3-phenyl-4-[(phenylamino) carbonyl]-1H-pyrrole-1-heptanoic acid.

STEP 8

Preparation of [R- (R*, R*)]-2-(4-Fluorophenyl)-β,δ-dihydroxy-5-(1-methylethyl)-3-phenyl-4-[(phenylamino)carbonyl]-1H-pyrrole-1-heptanoic acid, hemi calcium salt In a separate 200 mL beaker, calcium acetate (1.2 g, 7 mmol) is dissolved in water (20 mL). This calcium acetate solution is added to [R-(R*,R*)-]2-(4- fluorophenyl )-β, δ-dihydroxy-5 -(1-methylethyl)-3-phenyl-4-[(phenylamino)carbonyl]-1H-pyrrole-1-heptanoic acid, sodium salt solution and stirred at room temperature for 2 hours. The resultant solution is cooled to 10° C. for about 3 hours. The white solid is collected by filtration, washed with cold water, and is confirmed as [R-(R*,R*)]-2-(4-fluorophenyl)-β,δ-dihydroxy-5-(1-methylethyl)-3-phenyl-4-[(phenylamino)carbonyl]-1H-heptanoic, hemi calcium salt by High Performance Liquid Chromatography retention time comparison.

HPLC conditions:
Column: Ultramex CI8, 5u (250×4.6 ram).
Mobil phase: 22% MeCN:12% THF:66% 0.05 M NH$_4$H$_2$PO$_4$ pH =5 with NH$_4$OH
Flow rate: 1.5 mm/min
Detector: 254 nm
Retention time: 44.9–45.1.

EXAMPLE 2

]R-(R*,R*)]-2-(4-Fluorophenyl)-β,δ-dihydroxy-5-(1-methylethyl)-3-phenyl-4-[(phenylamino)carbonyl]-1H-pyrrole-1-heptanoic acid, hemi calcium salt Preparation of
(4R-cis)-6-(2-aminoethyl)-2,2-dimethyl-N,N-bis(-phenylmethyl)-1,3-dioxane-4-acetamide To a stirred −10° C. solution of N,N-bis(phenylmethyl)acetamide (prepared from N,N-bis(phenylmethyl)amine and acetyl chloride by refluxing for 2 hours in toluene) (120 g, 0.5 mol) in tetrahydrofuran (0.5 L) is slowly added a solution of lithium diisopropylamide in tetrahydrofuran-heptane (0.25 L of 2 M) while maintaining the temperature between −30° C. to −45° C., and the mixture is stirred at −20° C. to −30° C. for 30 minutes. (R)-4-cyano-3-hydroxybutyric acid, ethyl ester (Brower, supra) (20 g, 0.125 mol) as a solution in 200 mL of tetrahydrofuran is then added to the previous mixture. The reaction mixture is stirred for 30 minutes at −35° C. to −20° C., and transferred to a 2.2N aqueous hydrochloric acid solution (0.5 L). The aqueous layer is extracted with 300 mL of ethyl acetate, the aqueous layer is separated and reextracted with 100 mL of ethyl acetate, the extracts are combined and concentrated in vacuo to afford crude (R)-6-cyano-5-hydroxy-3-oxo-N,N-bis(phenylmethyl)hexanamide as an oil. This oil, approximately 0.1 mol, is dissolved in tetrahydrofuran (200 mL) and methanol (100 mL) under a nitrogen atmosphere. The solution is cooled to −20° C., and a 50% solution of methoxydiethylborane in tetrahydrofuran (50 mL) is added. The reaction is cooled to −78° C., and sodium borohydride (12 g, 0.32 mol) is added over 30 minutes. The reaction is maintained at −78° C. for 5 hours and allowed to warm to room temperature and stand for 10 hours under a nitrogen atmosphere. The reaction is quenched by the addition of acetic acid (20 mL) and concentrated by vacuum distillation to an oil. The residue is dissolved with methanol (300 mL), concentrated by vacuum distillation, redissolved with methanol (300 mL), and reconcentrated by vacuum distillation to give a yellow oil. The oil is taken up in ethyl acetate (300 mL) and washed with deionized water (300 mL). The ethyl acetate solution is concentrated by vacuum distillation to give crude [R-(R*,R*)]-6-cyano-3,5-dihydroxy-N,N-bis(phenylmethyl)hexanamide as an oil which is used without further purification; Molecular weight: 352. GC/MS m/e 352, 197, 179, 120, 106, 91, 77, 65, 51, 39.

The crude oil, approximately 0.09 mol, is dissolved in 2,2-dimethoxypropane (100 mL, 1.0 mol) and acetone (200 mL). Methanesulfonic acid (0.4 mL) is added, and the solution is stirred for 2 hours at room temperature. The reaction is quenched by the addition of aqueous sodium bicarbonate (500 mL) and ethyl acetate (300 mL). The ethyl acetate solution is concentrated by vacuum distillation to give 32.1 g of (4R-cis)-6-(cyanomethyl)-2,2-dimethyl-N,N-bis(phenylmethyl)-1,3-dioxane-4-acetamide as an oil; Molecular weight: 392. GC/MS m/e 392, 239, 196, 148, 106, 91, 79, 65, 43, 32.

A solution of (4R-cis)-6-(cyanomethyl)-2,2-dimethyl-N,N-bis(phenylmethyl)-1,3-dioxane-4-acetamide (10.0 g, 0.025 mol) in methanol (150 mL) containing anhydrous ammonia (2.25 g) is reacted with hydrogen gas in a Parr shaker at 30° C. in a presence of a slurry of Raney nickel A-7000 (3.7 g). After 3 hours, uptake of hydrogen has ceased, the mixture is cooled to 20° C., the atmosphere is vented and exchanged for nitrogen, the slurry is filtered through celite, and concentrated at reduced pressure to give 9.4 g of (4R-cis)-6-(2-aminoethyl)-2,2-dimethyl-N,N-bis(phenylmethyl)-1,3-dioxane-4-acetamide as an oil;

$^1$H-NMR (DMSO) δ1.26 (s, 3H), 1.41 (s, 3H), 2.12 (m, 1H), 2.5 (m, 1H), 3.11 (m, 2H), 3.23 (m, 2H), 3.35 (m, 2H), 4.44 (m, 2H), 4.48 (m, 2H), 4.52 (m, 4H), 7.3–7.5 (s, 10H).

In a process analogous to Example 1, (4R-cis)-6-(2-aminoethyl) -2,2-dimethyl-N,N-bis(phenylmethyl)-1,3-dioxane-4-acetamide is converted to [R-(R*,R*)]-5-(4-fluorophenyl)-β, δ-dihydroxy-2-(1-methylethyl)-4-phenyl-3-[(phenylamino)carbonyl]-N,N-bis(phenylmethyl)-1H-pyrrole-1-heptanamide which is further converted to [R-(R*,R*)]-2-(4-fluorophenyl)-β,δ-dihydroxy-5-(1-methylethyl)- 3-phenyl-4-[(phenylamino)-carbonyl]-1H-pyrrole-1-heptanoic acid, hemi calcium salt.

EXAMPLE 3

[R-(R*,R*)]-2-(4- Fluorophenyl)-β, δ-dihydroxy-5-(1-methylethyl)-3-phenyl-4-[(phenylamino)carbonyl]-1H-pyrrole-1-heptanoic acid, hemi calcium salt

Preparation of (4R-cis)-6-(2-aminoethyl)-N,N-diethyl-2,2-dimethyl-1,3-dioxane-4-acetamide To a stirred −10° C. solution of N,N-diethylacetamide (prepared from N,N-diethylamine and acetyl chloride by refluxing for 2 hours in toluene) (28.75 g, 0.25 mol) in tetrahydrofuran (0.25 L) is slowly added a solution of lithium diisopropylamide in tetrahydrofuran-heptane (0.125 L of 2M) while maintaining the temperature between −10° C. to −5° C., and the mixture is stirred at −20° C. to 0° C. for 30 minutes. (R)-4-cyano-3-hydroxybutyric acid, ethyl ester (Brower, supra) (10 g, 0.06 mol) as a solution in 200 mL of tetrahydrofuran is added to the previously prepared mixture. The reaction mixture is stirred for 30 minutes at −5° C. to −20° C., and transferred to a 2.2N aqueous hydrochloric acid solution (0.25 L). The aqueous layer is extracted with 300 mL of ethyl acetate, the aqueous layer is separated and reextracted with 50 mL of ethyl acetate, the extracts are combined and concentrated in vacuo to afford crude (R)-6-cyano-N,N-diethyl-5-hydroxy-3-oxohexanamide as an oil; Molecular weight: 226. GC/MS m/e 226, 157, 140, 114, 72, 58, 32.

This oil, approximately 0.05 mol, is dissolved in tetrahydrofuran (200 mL) and methanol (100 mL) under a nitrogen atmosphere. The solution is cooled to −20° C., and a 50% solution of methoxydiethylborane in tetrahydrofuran (30 mL) is added. The reaction is cooled to −78° C., and sodium borohydride (6 g, 0.15 mol) is added over 30 minutes. The reaction is maintained at −78° C. for 5 hours, allowed to warm to room temperature, and stand for 10 hours under a nitrogen atmosphere. The reaction is quenched by the addition of acetic acid (10 mL) and concentrated in vacuo to an oil. The residue is dissolved with methanol (200 mL), concentrated by vacuum distillation, redissolved with methanol (250 mL), and reconcentrated by vacuum distillation to give a yellow oil. The oil is taken up in ethyl acetate (300 mL), and washed with deionized water (300 mL). The ethyl acetate solution is concentrated in vacuo to give [R-(R*,R*)]-6-cyano-N,N-diethyl-3,5-dihydroxyhexanamide as an oil which is used without further purification; Molecular weight: 228. GC/MS m/e 228, 168, 100, 72, 43.

The oil, approximately 0.05 mol, is dissolved in 2,2-dimethoxypropane (50 mL, 0.5 mol) and acetone (100 mL). Methanesulfonic acid (0.3 mL) is added, and the solution is stirred for 2 hours at room temperature. The reaction is quenched by the addition of aqueous sodium bicarbonate (300 mL) and ethyl acetate (300 mL). The ethyl acetate layer is concentrated in vacuo to give 12.4 g of (4R-cis)-6-(cyanomethyl)- N,N-diethyl-2,2-dimethyl-1,3-dioxane-4-acetamide as an oil; Molecular weight: 268. GC/MS m/e 268, 253, 210, 170, 100, 72, 43.

A solution of (4R-cis) -6-(cyanomethyl)-N,N-diethyl-2,2-dimethyl-1,3-dioxane-4-acetamide (10.0 g, 0,037 mol) in methanol (220 mL) containing anhydrous ammonia (3.25 g) is reacted with hydrogen gas in a Parr shaker at 30° C. in a presence of a slurry of Raney nickel A- 7000 (4.2 g). After 3 hours, uptake of hydrogen has ceased, the mixture is cooled to 20° C., the atmosphere is vented and exchanged for nitrogen, the slurry is filtered through celite, and concentrated at reduced pressure to give 9.2 g of (4R-cis)-6-(2-aminoethyl)-N,N-diethyl-2,2-dimethyl-1,3-dioxane-4-acetamide as an oil.

In a process analogous to Example 1, (4R-cis)-6-(2-aminoethyl)-N,N-diethyl-2,2-dimethyl-1,3-dioxane-4-acetamide is converted to [R-(R*,R*)]-N,N-diethyl-5-(4- fluorophenyl)-β, δ-dihydroxy-2-(1-methylethyl)-4-phenyl-3-[(phenylamino) carbonyl]-1H-pyrrole-1-heptanamide which is further converted to [R- (R*,R,)]-2-(4-fluorophenyl)-β, δ-dihydroxy-5-(1-methylethyl)-3-phenyl-4-[(phenylamino) carbonyl]-1H-pyrrole-1-heptanoic acid, hemi calcium salt.

EXAMPLE 4

[R-(R*,R*)]-2-(4-Fluorophenyl)-β,δ-dihydroxy-5-(1-methylethyl)-3-phenyl-4-[(phenylamino)carbonyl]-1H-pyrrole-1-heptanoic acid, hemi calcium salt

Preparation of (4R-cis)-6-(2-aminoethyl)-N-butyl-N,N,2,2-trimethyl-1,3-dioxane-4-acetamide To a stirred −10° C. solution of N,N-n-butylmethylacetamide (prepared from N,N-n-butylmethylamine and acetyl chloride by refluxing for 2 hours in toluene) (65 g, 0.5 mol) in tetrahydrofuran (0.5 L) is slowly added a solution of lithium diisopropylamide in tetrahydrofuran-heptane (0.25 L of 2 M) while maintaining the temperature between −40° C. to −50° C., and the mixture is stirred at −20° C. to −30° C. for 30 minutes.

(R)-4-cyano-3-hydroxybutyric acid, ethyl ester (Brower, supra) (20 g, 0,125 mol) as a solution in 200 mL of tetrahydrofuran is then added to the previous mixture. The reaction mixture is stirred for 30 minutes at −25° C. to −20° C., and transferred to a 2.2N aqueous hydrochloric acid solution (0.5 L). The aqueous layer is extracted with 300 mL of ethyl acetate, the aqueous layer is separated and reextracted with 100 mL of ethyl acetate, the extracts are combined and concentrated in vacuo to afford crude (R)-N-butyl-6-cyano-5-hydroxy-N-methyl-3-oxohexanamide as an oil.

The oil, approximately 0.1 mol, is dissolved in tetrahydrofuran (200 mL) and methanol (100 mL) under a nitrogen atmosphere. The solution is cooled to −20° C., and a 50% solution of methoxydiethylborane in tetrahydrofuran (50 mL) is added. The reaction is cooled to −78° C., and sodium borohydride (12 g, 0.32 mol) is added over 30 minutes. The reaction is maintained at −78° C. for 5 hours and allowed to warm to room temperature and stand for 10 hours under a nitrogen atmosphere. The reaction is quenched by the addition of acetic acid (20 mL) and concentrated in vacuo to an oil. The residue is dissolved with methanol (300 mL), concentrated by vacuum distillation, redissolved with methanol (300 mL), and reconcentrated in vacuo to give a yellow oil. The oil is taken up in ethyl acetate (300 mL) and washed with deionized water (300 mL). The ethyl acetate solution is concentrated by vacuum distillation to give crude [R-(R*,R*)]-N-butyl-6-cyano-3,5-dihydroxy-N-methylhexanamide as an oil which is used as is.

The oil, approximately 0.1 mol, is dissolved in 2,2-dimethoxypropane (100 mL, 1.0 mol) and acetone (200 mL). Methanesulfonic acid (0.5 mL) is added, and the solution is stirred for 2 hours at room temperature. The reaction is quenched by the addition of aqueous sodium bicarbonate (400 mL) and ethyl acetate (300 mL). The ethyl acetate solution is concentrated by vacuum distillation to give 26.5 g of (4R-cis)-N-butyl-6-(cyanomethyl)-N,2,2-trimethyl-1,3-dioxane-4-acetamide as an oil; Molecular weight: 282. GC/MS m/e 282, 267, 207, 184, 154, 114, 87, 57, 44.

A solution of this nitrile (10.0 g, 0.035 mol) in methanol (183 mL) containing anhydrous ammonia (2.75 g) is reacted with hydrogen gas in a Parr shaker at 30° C. in the presence of a slurry of Raney nickel A-7000 (4.2 g). After 3 hours, uptake of hydrogen has ceased, the mixture is cooled to 20° C., the atmosphere is vented and exchanged for nitrogen, the slurry is filtered through celite, and concentrated in vacuo to give 9.25 g of (4R-cis)-6-(2-aminoethyl)-N-butyl-N,2,2-trimethyl-1,3-dioxane-4-acetamide as an oil.

In a process analogous to Example 1, (4R-cis)-6-(2-aminoethyl)-N-butyl-N,2,2-trimethyl-1,3-dioxane-4-acetamide is converted to [R-(R*,R*)]-N-butyl-5-(4-fluorophenyl)-β, δ-dihydroxy-N-methyl-2-(1-methylethyl)-4-phenyl-3-[(phenylamino)carbonyl]-1H-pyrrole-1-heptanamide which is further converted to [R-(R*,R*)]-2-(4-fluorophenyl)-β,δ-dihydroxy-5-(1-methylethyl)-3-phenyl-4-[(phenylamino)carbonyl]-1H-pyrrole-1-heptanoic acid, hemi calcium salt.

EXAMPLE 5

[R-(R*,R*)]-2-(4-Fluorophenyl)-β, δ-dihydroxy-5-(1-methylethyl)-3-phenyl-4-[(phenylamino)carbonyl]-1H-pyrrole-1-heptanoic acid, hemi calcium salt Preparation of (4R-cis)-6-(2-aminoethyl)-N-(1,1-dimethylethyl)-2,2-dimethyl-N-(phenylmethyl)-1,3-dioxane-4-acetamide To a stirred −10° C. solution of N-1,1-dimethylethyl, N-phenylmethylacetamide (prepared from N-1,1-dimethylethyl, N-phenylmethyl amine, and acetyl chloride by refluxing for 2 hours in toluene) (102.5 g, 0.5 mol) in tetrahydrofuran (0.5 L) is slowly added a solution of lithium diisopropylamide in tetrahydrofuran-heptane (0.25 L of 2 M) while maintaining the temperature between −40° C. to −50° C., and the mixture is stirred at −20° C. to −30° C. for 30 minutes. (R)-4-cyano-3-hydroxybutyric acid, ethyl ester (Brower, supra) (20 g, 0,125 mol) as a solution in 200 mL or tetrahydrofuran is then added to the previous mixture. The reaction mixture is stirred for 30 minutes at −25° C. to −20° C., and transferred to a 2.2N aqueous hydrochloric acid solution (0.5 L). The aqueous layer is extracted with 300 mL of ethyl acetate, the aqueous layer is separated and reextracted with 100 mL of ethyl acetate, the extracts are combined and concentrated in vacuo to afford crude (R)-6-cyano-N-(1,1-dimethylethyl)-5-hydroxy-3-oxo-N-(phenylmethyl)hexanamide as an oil.

The oil, approximately 0.1 mol, is dissolved in tetrahydrofuran (150 mL) and methanol (80 mL) under a nitrogen atmosphere. The solution is cooled to −20° C., and a 50% solution of methoxydiethylborane in tetrahydrofuran (75 mL) is added. The reaction is cooled to −78° C., and sodium borohydride (12 g, 0.32 mol) is added over 30 minutes. The reaction is maintained at −78° C. for 5 hours and allowed to warm to room temperature and stand for 10 hours under a nitrogen atmosphere. The reaction is quenched by the addition of acetic acid (20 mL) and concentrated in vacuo to an oil. The residue is dissolved in methanol (300 mL), concentrated by vacuum distillation, redissolved in methanol (200 mL), and reconcentrated in vacuo to give a yellow oil.

The oil is taken up in ethyl acetate (300 mL) and washed with deionized water (300 mL). The ethyl acetate solution is concentrated by vacuum distillation to give crude [R-(R*,R*)]-6-cyano-N-(1,1-dimethylethyl)-3,5-dihydroxy-N-(phenylmethyl)hexanamide as an oil which is as is; Molecular weight 318. GC/MS m/e 318, 299, 261, 243, 220, 204, 178, 148, 106, 91, 65, 57, 41.

The oil, approximately 0.09 mol, is dissolved in 2,2-dimethoxypropane (100 mL, 1.0 mol) and acetone (200 mL). Methanesulfonic acid (0.5 mL) is added, and the solution is stirred for 2 hours at room temperature. The reaction is quenched by the addition of aqueous sodium bicarbonate (400 mL) and ethyl acetate (300 mL). The ethyl acetate solution is concentrated in vacuo to give 27.6 g of (4R-cis)-6-(cyanomethyl)-N-(1,1-dimethylethyl)-2,2-dimethyl-N-(phenylmethyl)-1,3-dioxane-4-acetamide as an oil.

A solution of this nitrile (5.0 g, 0.012 mol) in methanol (70 mL) containing anhydrous ammonia (1.05 g) is reacted with hydrogen gas in a Parr shaker at 30° C. in a presence of a slurry of Raney nickel A-7000 (2.5 g) . After 3 hours, uptake of hydrogen has ceased, the mixture is cooled to 20° C., the atmosphere is vented and exchanged for nitrogen, the slurry is filtered through celite, and concentrated in vacuo to give 4.2 g of (4R-cis)-6-(2-aminoethyl)-N-(1,1-dimethylethyl)-2,2-dimethyl-N-(phenylmethyl)-1,3-dioxane-4-acetamide as an oil; Molecular weight 358. GC/MS m/e 358, 343, 301, 287, 260, 243, 227, 204, 176, 148, 132, 91, 84, 57, 43.

In a process analogous to Example 1 (4R-cis)-6-(2-aminoethyl)-N-(1,1-dimethylethyl)-2,2-dimethyl-N-(phenylmethyl)-1,3-dioxane-4- acetamide is converted to [R-(R*, R*)]-N-(1,1-(dimethylethyl)-5-(4-fluorophenyl)-β,δ-dihydroxy-2-(1-methylethyl)-4-phenyl-3-[(phenylamino)carbonyl]-N-(phenylmethyl)-1H-pyrrole-1-heptanamide which is further converted to [R-(R*,R*)]-2-(4-fluorophenyl)-β, δ-dihydroxy-5-(1-methylethyl)-3-phenyl-4-[(phenylamino)carbonyl]-1H-pyrrole- 1 -heptanoic acid, hemi calcium salt.

EXAMPLE 6

[R-(R*,R*)]-2-(4-Fluorophenyl)-β, δ-dihydroxy-5-(1-methylethyl)-3-phenyl-4-[(phenylamino)carbonyl]-1H-pyrrole-1-heptanoic acid, hemi calcium salt Preparation of (4R-cis)-1-[[6-(2-aminoethyl)-2,2-dimethyl-1,3-dioxan-4-yl]acetyl]piperidine To a stirred −10° C. solution of 1-acetylpiperidine (127 g, 1.0 mol) in tetrahydrofuran (1.0 L) is slowly added a solution of lithium diisopropylamide in tetrahydrofuran-heptane (0.5 L of 2 M) while maintaining the temperature between −40° C. to −50° C., and the mixture is stirred at −20° C. to −30° C. for 30 minutes. (R)-4-cyano-3-hydroxybutyric acid, ethyl ester (Brower, supra) (40 g, 0.25 mol) as a solution in 200 mL of tetrahydrofuran is then added to the previous mixture. The reaction mixture is stirred for 30 minutes at −25° C. to −20° C., and transferred to a 2.2N aqueous hydrochloric acid solution (1L). The aqueous layer is extracted with 500 mL of ethyl acetate, the aqueous layer is separated and extracted with 100 mL of ethyl acetate, the extracts are combined and concentrated in vacuo to afford (R)-ε-hydroxy-α,γ-dioxo-1-piperidineheptanenitrile as an oil.

The oil, approximately 0.2 mol, is dissolved in tetrahydrofuran (200 mL) and methanol (100 mL) under a nitrogen atmosphere. The solution is cooled to −20° C., and a 50% solution of methoxydiethylborane in tetrahydrofuran (105 mL) is added. The reaction is cooled to −78° C., and sodium borohydride (24 g, 0.63 mol) is added over 30 minutes. The reaction is maintained at −78° C. for 5 hours and allowed to warm to room temperature and stand for 10 hours under a nitrogen atmosphere. The reaction is quenched by the addition of acetic acid (40 mL) and concentrated in vacuo to an oil. The residue is dissolved with methanol (400 mL), concentrated by vacuum distillation, redissolved with methanol (300 mL), and reconcentrated by vacuum distillation to give a yellow oil. The oil is taken up in ethyl acetate (300 mL) and washed with deionized water (500 mL). The ethyl acetate solution is concentrated in vacuo to give [R-(R*, R*)]-γ,ε-dihydroxy-α-oxo-1-piperidineheptanenitrile as an oil which is used as is; Molecular weight 318. GC/MS m/e 318, 299, 261, 243, 220, 204, 178, 148, 106, 91, 65, 57, 41.

The oil, approximately 0.18 mol, is dissolved in 2,2-dimethoxypropane (160 mL, 1.5 mol) and acetone (300 mL). Methanesulfonic acid (0.5 mL) is added, and the solution is stirred for 2 hours at room temperature. The reaction is quenched by the addition of aqueous sodium bicarbonate (800 mL) and ethyl acetate (500 mL). The ethyl acetate solution is concentrated in vacuo to give 47.5 g of (4R-cis)- 1-[[6-(cyanomethyl)-2,2-dimethyl-1,3-dioxan-4-yl]acetyl]piperidine as an oil; Molecular weight 280. GC/MS m/e 280, 265, 240, 222, 205, 182, 164, 154, 127, 112, 96, 84, 69, 43, 32.

A solution of the nitrile (5.0 g, 0.017 mol) in methanol (100 mL) containing anhydrous ammonia (1.5 g) is reacted with hydrogen gas in a Parr shaker at 30° C. in the presence of a slurry of Raney nickel A-7000 (3.8 g). After 3 hours, uptake of hydrogen has ceased, the mixture is cooled to 20° C., the atmosphere is vented and exchanged for nitrogen, the slurry is filtered through celite, and concentrated in vacuo to give 4.85 g of (4R-cis)-1-[[6-(2-aminoethyl)-2,2-dimethyl-1,3-dioxan-4-yl]acetyl]piperidine as an oil.

In a process analogous to Example I (4R-cis)-1-[[6-(2-aminoethyl)-2,2-dimethyl-1,3-dioxan-4-yl]acetyl]piperidine is converted to [R-(R*,R*)]1-[3,5-dihydroxy-7-oxo-7-(1-piperidinyl)heptyl]-5-(4-fluorophenyl-2-(1-methylethyl)-N-4-diphenyl-1H-pyrrole-3-carboxamide which is further converted to [R-(R*,R*)]-2-(4-fluorophenyl)-β,δ-dihydroxy-5-(1-methylethyl)-3-phenyl-4-[(phenylamino)carbonyl]-1H-pyrrole- 1-heptanoic acid, hemi calcium salt.

We claim:

1. A compound of Formula II

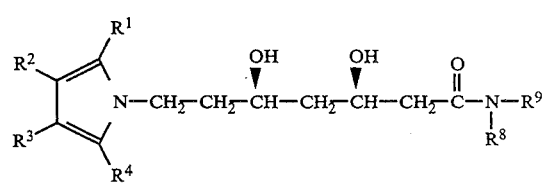

wherein $R^1$ is
1-naphthyl,
2-naphthyl,
cyclohexyl,
cyclohexylmethyl,
norbornenyl,
phenyl,
phenyl substituted with
fluorine,
chlorine,
bromine,
hydroxyl,
trifluoromethyl,
alkyl of from one to four carbon atoms,
alkoxy of from one to four carbon atoms, or
alkanoyloxy of from two to eight carbon atoms,
benzyl,
2-,3-, or 4-pyridinyl, or
2-, 3-, or 4-pyridinyl-N-oxide;
$R^2$ or $R^3$ is independently
hydrogen,
alkyl of from one to six carbon atoms,
cyclopropyl,
cyclobutyl,
cyclopentyl,
cyclohexyl,
phenyl,
phenyl substituted with
fluorine,
chlorine, bromine,
hydroxyl,
trifluoromethyl,
alkyl of from one to four carbon atoms, or
alkoxy of from one to four carbon atoms,
cyano,
trifluoromethyl, or —$CONR^5R^6$ where $R^5$ and $R^6$ are
   independently
hydrogen,
alkyl of from one to six carbon atoms,
phenyl,
phenyl substituted with
   fluorine,
   chlorine,
   bromine,
   cyano, or
   trifluoromethyl;
$R^4$ is
   alkyl of from one to six carbon atoms,
   cyclopropyl,
   cyclobutyl,
   cyclopentyl,
   cyclohexyl, or
   trifluoromethyl; and
$R^8$ or $R^9$ is independently
   alkyl of from one to ten carbon atoms,
   cyclopropyl,
   cyclobutyl,
   cyclopentyl
   cyclohexyl,
   benzyl or
   phenyl or
   $R^e$ and $R^9$ together are
      —$(CH_2)_4$—,
      —$(CH_2)_5$—,
      —$(CH(R^{10})$—$CH_2)_3$—,
      —$(CH(R^{10})$—$CH_2)_4$—,
      —$(CH(R^{10})$—$(CH_2)_2$—$CH(R^{10}))$—,
      —$(CH(R^{10})$—$(CH_2)_3$—$CH(R^{10}))$—,
      —$CH_2$—$CH_2$—O—$CH_2$—$CH_2$—,
      CH $(R^{10})$—$CH_2$—O—$CH_2$—$CH_2$—,
      —$CH(R^{10})$—$CH_2$—O—$CH(R^{10})$—,
wherein $R^{10}$ is alkyl of from one to four carbon atoms
provided $R^8$ and $R^9$ are not both methyl.

2. A compound according to claim 1 wherein $R^8$ and $R^9$ are phenyl.

3. A compound according to claim 1 wherein $R^8$ and $R^9$ are phenylmethyl.

4. A compound according to claim 1 wherein $R^8$ and $R^9$ are combined as —$(CH_2)_5$—.

5. A compound according to claim 1 wherein $R^8$ is butyl and $R^9$ is methyl.

6. A compound according to claim 1 wherein $R^8$ is 1,1-dimethylethyl and $R^9$ is phenylmethyl.

7. A compound according to claim 1 wherein $R^8$ and $R^9$ are ethyl.

8. A compound according to claim 1 selected from the group consisting of:
[R-(R*,R*)]-5-(4-fluorophenyl)-$\beta$,$\delta$-dihydroxy-2-(1-methylethyl)-N,N,4-triphenyl-3-[(phenyl amino)carbonyl]- 1H-pyrrole-1-heptanamide;
[R-(R*,R*)]-N,N-diethyl-5-(4-fluorophenyl)-$\beta$,$\delta$-dihydroxy-2-(1-methylethyl)-4-phenyl- 3-[(phenylamino)carbonyl]-1H-pyrrole-1-heptanamide;
[R-(R*,R*)]-5-(4-fluorophenyl)-$\beta$, $\delta$-dihydroxy-2-(1-methylethyl)-4-phenyl-3-[(phenylamino)carbonyl]-N,N-bis(phenylmethyl)-1H-pyrrole-1-heptanamide;
[R-(R*,R*)]-N-butyl-5-(4-fluorophenyl)-$\beta$,$\delta$dihydroxy-N-methyl-2-(1-methylethyl)-4-phenyl-3-[(phenylamino)carbonyl]-1H-pyrrole-1-heptanamide;
[R-(R*,R*)]-N-(1,1-dimethylethyl)-5-(4-fluorophenyl)-$\beta$, $\delta$-dihydroxy-2-(1-methylethyl)-4-phenyl-3-[(phenylamino)carbonyl]-N-(phenylmethyl)-1H -pyrrole-1- heptanamide;
[R-(R*,R*)]-1-[3,5-dihydroxy-7-oxo-7-(1-piperidinyl)heptyl]-5-(4-fluorophenyl)-2-(1-methylethyl)-N,4-diphenyl-1H-pyrrole-3- carboxamide; and
[R-(R*, R*)]-1-[3,5-dihydroxy-7-oxo-7-(1-pyrrolidinyl)heptyl]-5-(4-fluorophenyl)-2-(1-methylethyl)- N,4-diphenyl-1H-pyrrole-3-carboxamide.

9. A pharmaceutical composition adapted for administration as a hypolipidemic and hypocholesterolemic agent comprising a therapeutically effective amount of a compound according to claim 1 in admixture with a pharmaceutically acceptable excipient, diluent, or carrier.

* * * * *